United States Patent [19]

Irwin

[11] Plant 3,992

[45] Dec. 21, 1976

[54] KALANCHOE PLANT

[76] Inventor: Lawrence T. Irwin, P.O. Box 657, Canyon, Tex. 79015

[21] Appl. No.: 609,781

[22] Filed: Sept. 2, 1975

[51] Int. Cl.[2] ..... A01H 5/00
[52] U.S. Cl. ..... Plt./68
[58] Field of Search ..... Plt./68

*Primary Examiner*—Robert E. Bagwill
*Attorney, Agent, or Firm*—Frank B. Robb

CLAIM

A new and distinct variety of kalanchoe plant, substantially as herein shown and described, characterized particularly as to novelty by the unique combination of a short, compact and bushy, but upright, habit of growth; flexible foliage of medium size which is topped by a profusion of small reddish colored flowers that are borne on short, stocky flower stems; a distinctive, unusual and attractive Brick Red flower color; the ability to flower in a shorter time than most other kalanchoe varieties; a distinctive and pleasant lemony flower scent; and excellent suitability for potted plant use.

1 Drawing Figure

The present invention relates to a new and distinct variety of kalanchoe plant which was originated by me by crossing the kalanchoe variety known as "Gold Dust" (patent pending) with an unnamed and unpatented red, scented Hummel hybrid kalanchoe selection, the former being the seed parent and the latter being the pollen parent.

As the result of this breeding, I have produced a new and improved kalanchoe variety which is distinguished from its parents, as well as from all other kalanchoe varieties of which I am aware, as evidenced by the following unique combination of principal characteristics which are outstanding in the new variety and which make it a valuable addition to the line of kalanchoe varieties that are presently commercially available:

1. A short, compact and bushy, but upright, habit of growth;
2. Flexible foliage of medium size which is topped by a profusion of small reddish colored flowers that are borne on short, stocky flower stems;
3. A distinctive, unusual and attractive Brick Red flower color;
4. The ability to flower in a shorter time than most other kalanchoe varieties;
5. A distinctive and pleasant lemony flower scent; and
6. Excellent suitability for potted plant use.

Asexual reproduction of my new kalanchoe variety by means of cuttings, as performed by me in my greenhouses located at Canyon, Tex., shows that the foregoing characteristics and distinctions come true and are established and transmitted through succeeding propagations.

The accompanying drawing shows a typical blooming plant of my new variety, as well as a close-up view of the flowers, as depicted in color as nearly true as it is possible to make the same in a color illustration of this character.

The following is a detailed description of my new variety, with color terminology in accordance with The Exotica Horticultural Color Guide, published by Roehrs Company, except where general color terms of ordinary dictionary significance are obvious:

Parentage: Seedling.

*Seed parent.*—"Gold Dust".

*Pollen parent.*—An unnamed, selected Hummel hybrid.

Propagation: Holds its distinguishing characteristics through succeeding propagations by cuttings.

Locality where grown and observed: Canyon, Tex.

Plant:

*Form.*—Short; compact; bushy, but upright.

*Growth habit.*—Much-branched; self-branching; medium vigorous; about 10 inches to 12 inches tall.

*Rooting habit.*—Coordinate; roots easily from any part of stem, forming a fibrous root system.

*Blooming habit.*—Flowers naturally about Dec. 1, but usually from 7 to 10 days earlier than other newer varieties.

*Blooming season.*—Due to its short day response to flowering, this new variety can be brought into bloom the year around by appropriate photoperiodic manipulation; blooms in 10 to 11 weeks, as compared to 11 to 16 weeks for other varieties.

Foliage:

*Size.*—Medium; average about 3 inches long and about 2⅜ inches wide when mature.

*Quantity.*—Normal abundance.

*Color.*—New foliage—Upper side—Near Lettuce Green, No. 81+. Under side—Near Lettuce Green, No. 81. Old foliage—Upper side—Near Moss Green, No. 82. Under side—Near Moss Green, No. 82−.

*Shape.*—Basically oblong, with obtuse tip and truncate base.

*Texture.*—Upper side—Glossy and smooth. Under side—Smooth.

Disease resistance: Comparable to that of other newer hybrids which are more resistant than standard varieties, as determined by comparison with such other varieties grown in the same greenhouses under the same conditions at Canyon, Tex.

Flowers: Pistillate staminate; perfect complete.

*Size.*—Small. Diameter—About 7/16 inch. Depth—About ⅝ inch.

*Petals.*—Length—About ¼ inch. Width—About 3/16 inch.

*Form.*—Compound umbel; section petals united; ovary superior.

*Color.*—Upper side—New flowers—Near Brick Red, No. 20. Old flowers—Near Mandarin Red, No. 24, with a yellowish cast. Under side—New flowers—Near Apricot, No. 11. Old flowers—Near Apricot, No. 11. Throat of corolla—Near Canary Yellow, No. 3.

*Blooming period.*—From 4 to 5 weeks.

Fruit: None.

Hardiness: Good in range of 55° F. to 100° F. as grown in greenhouse.

General observations: The new variety has all the desirable qualities of a good pot plant with a flower color and scent that makes it unusual and distinctive in comparison with all other kalanchoe varieties.

I claim

1. A new and distinct variety of kalanchoe plant, substantially as herein shown and described, characterized particularly as to novelty by the unique combination of a short, compact and bushy, but upright, habit of growth; flexible foliage of medium size which is topped by a profusion of small reddish colored flowers that are borne on short, stocky flower stems; a distinctive, unusual and attractive Brick Red flower color; the ability to flower in a shorter time than most other kalanchoe varieties; a distinctive and pleasant lemony flower scent; and excellent suitability for potted plant use.

* * * * *

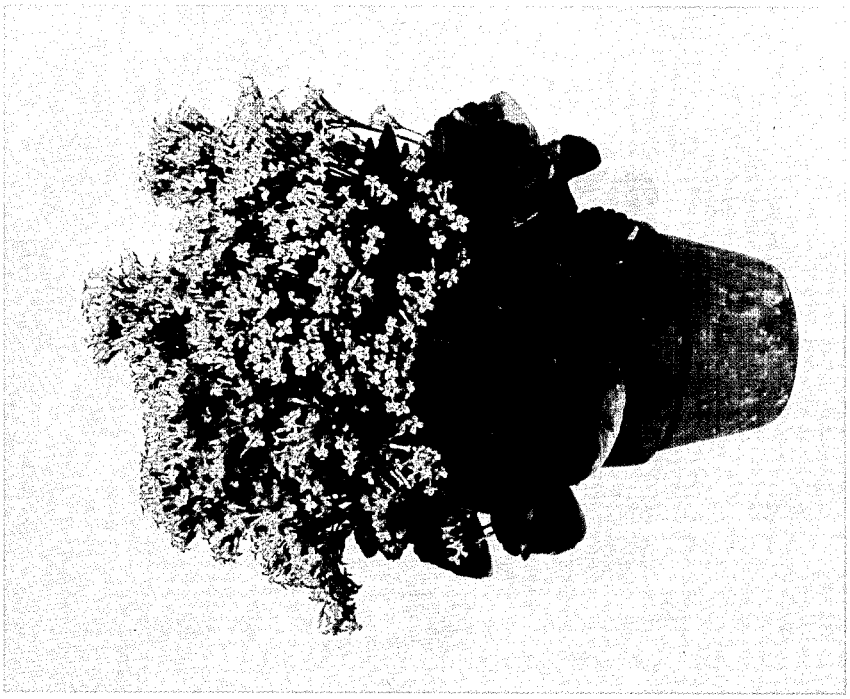
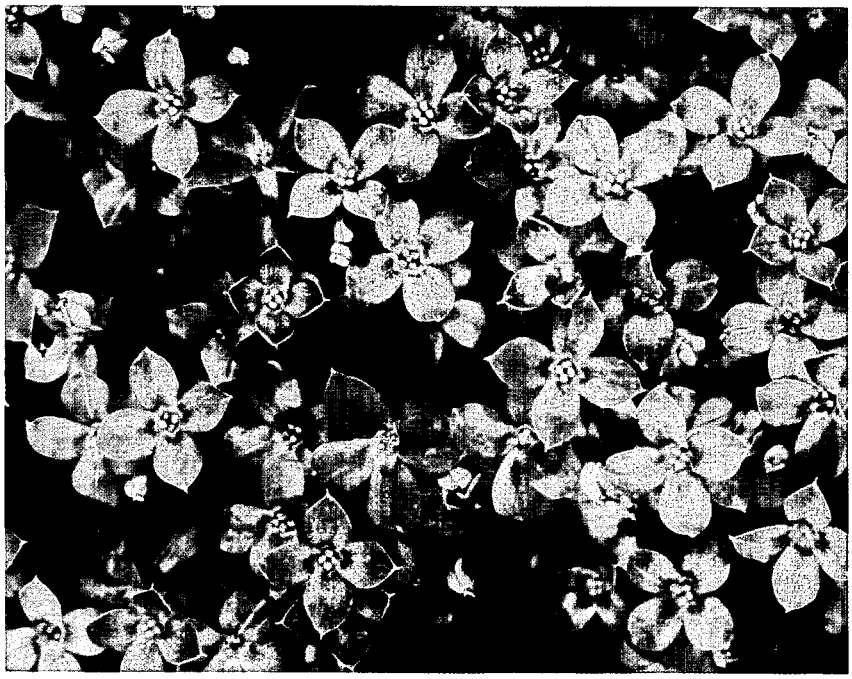

Dec. 21, 1976
L. T. IRWIN
KALANCHOE PLANT
Filed Sept. 2, 1975
Plant Pat. 3,992